(12) United States Patent
Bly

(10) Patent No.: US 11,172,871 B2
(45) Date of Patent: Nov. 16, 2021

(54) METHOD OF TREATMENT OF PRESSURE RELATED SKIN INJURY

(71) Applicant: Deborah C Bly, Chesterfield, MO (US)

(72) Inventor: Deborah C Bly, Chesterfield, MO (US)

( * ) Notice: Subject to any disclaimer, the term of this patent is extended or adjusted under 35 U.S.C. 154(b) by 0 days.

(21) Appl. No.: 15/862,358

(22) Filed: Jan. 4, 2018

(65) Prior Publication Data

US 2018/0125411 A1 May 10, 2018

Related U.S. Application Data

(63) Continuation of application No. 12/793,514, filed on Jun. 3, 2010, now abandoned.
(Continued)

(51) Int. Cl.
| | |
|---|---|
| *A61B 5/0205* | (2006.01) |
| *A61B 5/00* | (2006.01) |
| *G16H 50/30* | (2018.01) |
| *G16H 20/30* | (2018.01) |
| *G16H 50/20* | (2018.01) |
| *A61B 5/021* | (2006.01) |
| *A61B 5/024* | (2006.01) |
| *A61B 5/145* | (2006.01) |

(52) U.S. Cl.
CPC ............ *A61B 5/412* (2013.01); *A61B 5/0075* (2013.01); *A61B 5/441* (2013.01); *A61B 5/445* (2013.01); *A61B 5/447* (2013.01); *A61B 5/6843* (2013.01); *A61B 5/7275* (2013.01); *G16H 20/30* (2018.01); *G16H 50/20* (2018.01); *G16H 50/30* (2018.01); *A61B 5/021* (2013.01); *A61B 5/024* (2013.01); *A61B 5/14542* (2013.01); *A61B 2562/0247* (2013.01)

(58) Field of Classification Search
CPC ..................................................... A61B 5/445
See application file for complete search history.

(56) References Cited

U.S. PATENT DOCUMENTS

| | | | |
|---|---|---|---|
| 6,287,253 | B1 | 9/2001 | Ortega et al. |
| 7,536,214 | B2 | 5/2009 | Myers et al. |
| (Continued) | | | |

OTHER PUBLICATIONS

Papanikolaou et al. "Risk assessment scales for pressure ulcers: a methodological review." Int J Nurs Stud. Feb. 2007;44(2):285-96. Epub Dec. 4, 2006. (Year: 2006).*

(Continued)

*Primary Examiner* — Meredith Weare
(74) *Attorney, Agent, or Firm* — Sandberg Phoenix & von Gontard, P.C.

(57) ABSTRACT

A system or method for pressure related skin injury risk assessment and treatment including measuring extrinsic and intrinsic skin pressure of the patient through assigned ratings responsive to the skin pressure measurement, measuring oxygenation of the patient and assigning a rating responsive to the oxygenation measurement, measuring perfusion of the patient and assigning a rating responsive to the perfusion measurement, summing the skin pressure, oxygenation and perfusion ratings to obtain a POP Box score, determining a risk of pressure related skin injury for the patient in response to the POP Box score, and determining or selecting a recommended treatment from among a plurality of recommended treatments for the patient in response to the determined risk of pressure related skin injury.

20 Claims, 7 Drawing Sheets

Related U.S. Application Data

(60) Provisional application No. 61/183,667, filed on Jun. 3, 2009.

(56) References Cited

U.S. PATENT DOCUMENTS

| | | | |
|---|---|---|---|
| 7,553,285 | B2 | 6/2009 | Mao |
| 7,569,017 | B2 | 8/2009 | Mao |
| 7,570,979 | B2 | 8/2009 | Cooper |
| 7,582,060 | B2 | 9/2009 | Mao |
| 7,613,489 | B2 | 11/2009 | Myers |
| 8,116,838 | B2 | 2/2012 | Gaspard et al. |
| 2002/0082485 | A1 | 6/2002 | Faithfull et al. |
| 2003/0171954 | A1 | 9/2003 | Guerin et al. |
| 2004/0059199 | A1 | 3/2004 | Thomas et al. |
| 2005/0165284 | A1* | 7/2005 | Gefen .................... A61B 5/015 600/300 |
| 2006/0149154 | A1 | 7/2006 | Stephens et al. |
| 2006/0253160 | A1 | 11/2006 | Benditt et al. |
| 2007/0016079 | A1 | 1/2007 | Freemen et al. |
| 2008/0098333 | A1 | 4/2008 | Champion et al. |
| 2009/0076732 | A1 | 3/2009 | Sprigle et al. |
| 2011/0124987 | A1 | 5/2011 | Papazoglou et al. |
| 2011/0144462 | A1 | 6/2011 | Lifsitz et al. |

OTHER PUBLICATIONS

Nursebob, "Hemodynamics in Critical Care SvO2 Monitoring", Feb. 4, 2009, available at http://micunursing.com/svo2monitoring.htm.

"Hutchinson Technology Gets FDA Clearance for InSpectra StO2 Tissu Oxygenation Monitor", Wireless News, web page, Jul. 22, 2006, available at http://www.highbeam.com/doc/1P1-126612585.html.

Traumarn25, "Soo has any one heard of StO2??", All Nurses.com, web pages, Jan. 29, 2009, available at http://allnurses.com/ccu-nursing-forum/soo-has-any-366541.html.

ViOptix—Tissue Oximetry, "Assessing Tissue Viability with StO2 Enables Early Intervention to Improve Patient Outcomes", Sep. 9, 2009, available at http://www.vioptix/pdf/T.OxBrochure.pdf.

"Prevention Plus Home of the Braden Scale web pages", Bradenscale.com web page, available at http://www.bradenscale.com/products.htm.

ViOptix web pages, 2008, available at http://web.archive.org/web/20080501110217/www.vioptix.com/docs/home/home.asp.

National Pressure Ulcer Advisory Panel, The Unavoidable Outcome: A Pressure Injury Consensus Conference, Feb. 27, 2014, Pre-Conference Document: State of the Science.

Langemo DK, Brown G. Skin fails too: acute, chronic, and end-stage skin failure. Adv Skin Wound Care. 2006;19(4):206-211.

DeFloor T., The risk of pressure sores: a conceptual scheme. 1999 Blackwell Science Ltd., Journal of Clinical Nursing, (8) 206-216.

Waterlow J. Pressure sores; a risk assessment card. Nursing Times. 1985;81(48):49-55.

Compton F, Hoffmann F, Hortig T, et al. Pressure ulcer predictorsin ICU patients: nursing skin assessment versus abjective parameters [published correction appears in J Wound Care. 2008;17(11):493]. J Wound Care. 2008; 17(10):417-424.

Thomas DR. Prevention and treatment of pressure ulcers: what works? what doesn't? Cleve Clin J Med. 2001; 68(8):704-707, 710-720.

Reddy M, Gill SS, Pochon PA. Preventing pressure ulcers: a systematic review. JAMA. 2006;296(8):974-984.

De Laat EH, Pickkers P, Schoonhoven L, Verbeek AL, Feuth T,van Achterberg T. Guideline implementation results in a decrease of pressure ulcer incidence in critically ill patients.Crit Care Med. 2007;35(3):815-820, 966-967.

Nijs N, Toppets A, Defloor T, Bernaerts K, Milisen K, Van Den Berghe G. Incidence and risk factors for pressure ulcers in the intensive care unit. J Clin Nurs. 2008;18(9):1258-1266.

Reed RL, Hepburn K, Adelson R, Center B, McKnight P. Low serum albumin levels, confusion, and fecal incontinence: are these risk factors for pressure ulcers in mobility-impaired hospitalized adults? Gerontology. 2003;49(4):255-259.

Eachempati SR, Hydo LJ, Barie PS. Factors influencing the development of decubitus ulcers in critically ill surgical patients. Crit Care Med. 2001;29:1678-1682.

Suriadi, Sanada H, Sugama J, et al. Risk factors in the development of pressure ulcers in an intensive care unit in Pontianak, Indonesia. Int Wound J. 2007;4(3):208-215.

Suriadi, Sanada H, Sugama J, Thigpen B, Subuh M. Development of a new risk assessment scale for predicting pressure ulcers in an intensive care unit. Nurs Crit Care. 2008;13(1):34-43.

Randomized, controlled trial of alternating pressure mattresses compared with alternating pressure overlays for the prevention of pressure ulcers : PRESSURE (pressure relieving support surfaces) trial. BMJ, doi:10.1136/omj.38849.478299.7c (published Jun. 1, 2006).

Bergstrom N, Braden BJ, Laguzza A, Holman V. The Braden Scale for predicting pressure sore risk. Nurs Res. 1986;36(4): 205-210.

Nixon J, Cranny G, Bond S. Skin alterations of intact skin and risk factors associated with pressure ulcer development in surgical patients: a cohort study Int J Nurs Stud. 2007;44:655 663.

Curley et al. "Predicting pressure ulcer risk in pediatric patients: the Braden Q Scale." Nurs Res. Jan.-Feb. 2003;52(1):22-33.

Mayo Clinic. "Bedsores (Pressure Sores)." Jul. 12, 2008. http ://web. archive, o rg/web/200807120415191http://www, m ayoclin c. co mlhealthlbedsoreslDSOO5701D Section risk-factors.

Hutchinson Technology BioMeasurement Division. "StO2: Tissue Oxygen Saturation." 2013. W www.htibiomeasurement.comltechnologylsto2_tissue_oxygen_saturation/.

Royal College of Nursing. "Pressure Ulcer Risk Assessment and Prevention: Recommendations." Clinical Practice Guidelines. Apr. 2001.

Wywialowski EF. "Tissue perfusion as a key underlying concept of pressure ulcer development and treatment." J Vasc Nurs.Mar. 1999;17(1):12-16.

Jonsson et al. "Tissue oxygenation, anemia, and perfusion in relation to wound healing in surgical patients." Ann Surg. Nov. 1991; 214(5): 605-613.

Lamberts, SWJ. "The Value of Pressure Ulcer Risk Assessment and Interface Pressure Measurements in Patients: A nursing perspective." 2005. 160 pages.

Senturan et al. "The relationship among pressure ulcers, oxygenation, and perfusion in mechanically ventilated patients in an intensive care unit." J Wound Ostomy Continence Nurs. Sep.-Oct. 2009;36(5):503-8.

Hartford Institute for Geriatric Nursing. "Preventing pressure ulcers and skin tears. U In: Evidence-based geriatric nursing protocols for best practice." Jan. 2008.7 pages.

Curley et al. "Pressure ulcers in pediatric intensive care: incidence and associated factors." Pediatr Crit Care Meal. Jul. 2003;4(3):284-90.

Keller et al. "Pressure ulcers in intensive care patients: a review of risks and prevention." Intensive Care Med. 2002 W Oct;28(10):1379-88. Epub Sep. 7, 2002.

Maklebust, J. "Pressure Ulcers Etiology and Prevention." Nurs Clin North Am. Jun. 1987;22(2):359-77.

\* cited by examiner

Pressure, Oxygenation, and Perfusion (POP) Box Factor Assessment

Persons Name: _____    Date: _____

| Factor/Variable | Rating of 1 | Rating of 2 | Rating of 3 | Rating of 4 | POP Factor Assessment (POP FAV) |
|---|---|---|---|---|---|
| A. Braden Scale | 17-15 | 14-12 | 12-10 | 9 and below | |
| B. Patient Age | 20-40 years old | 40-60 years old | 60-80 years old | Greater than 80 | |
| C. Body Mass Index (BMI) | Normal weight but Braden compromised below 16 | Underweight = <18.5 | Overweight = 25-29.9 | Obese = BMI of 30 or greater | |
| D. Found Down | short period of time less than 1 hour | 1 to 2 hours wherein the ph and lactate may/or may not be affected | 2 to 5 hours wherein ph is down and lactate up | Greater than 5 hours wherein ph is down and lactate up, with potentially MB-CPK also up | |
| E. Vital sign instability | HR WNL, SBP <90 DBP<60, MAP <60 | HR >100, SBP <85 DBP<50, MAP <55 | HR >120, SBP <70 DBP <45, MAP <50 | HR in/out >140, SBP 70 or less with tacky; DBP and MAP critically low | |
| F. Pressor Agents, e.g., vaso active agents | Dopamine at 5mcg/kg/min or Levophed 5-10mcg/min | Dopamine 10-15mcg/kg/min or Levophed 10-15mcg/min | Dopamine 15-25 mcg/kg/min or Levophed 15-25 mcg/min | Dopamine ineffective or Levophed >25mcg/min | |
| G. SvO2 or ScvO2 | SvO2 <60 or >75 | SvO2 40-50 cardiogenic /75-80 septic shock | SvO2 <40 cardiogenic/ 80-90 septic shock | SvO2 <30cardiogenic shock/>90 septic shock | |
| H. P/F Ratio | P/F ratio 280-250 | P/F ratio 250-200 | P/F 200-150 | P/F <150 | |

FIG. 1A

Page 1 of 5

Pressure, Oxygenation, and Perfusion (POP) Box Factor Assessment

FIG. 1B

| | Recovery time 1-2 minutes | Recovery time 2-5 minutes | Recovery time 5-10 minutes | Recovery time > 10 minutes | |
|---|---|---|---|---|---|
| I. Desaturation Recovery time (SpO2 90 or less) | | | | | |
| J. CO/CI/SV | CI-2.5 BNP >100 SV > 60 | CI <2.0 BNP >200 60<SV>55 | CI <1.5 BNP >500 55<SV>50 | CI <1.0 BNP >800 SV<50 | |
| K. Massive edema-Sepsis fluid resuscitation, acute renal failure (ARF), and low albumin | Edema considered to be +1 mm with finger compression | Edema considered to be +2mm with finger compression | Edema considered to be +3mm with finger compression | Edema considered to be +4 or greater with finger compression | |
| L. Operating Room Procedure Variables:<br>  a. time on OR table > 4 hours- especially w/o pressure reducing device<br>  b. Chilling of core temp – decrease bleeding<br>  d. Not placed on pressure reducing surface while reperfusion<br>  d. Drop of MAP < 55<br>  e. Use of Neo stick or presser agent to recover B/P<br>  f. Use of Heart-Lung bypass machine<br>  g. PAR instability<br>  h. excessive bleeding (can be defined by way of example as bleeding greater than 6 U of PRBC's required in a 24 hour perioperative period). | 1-2 variables present | 3-4 variables present | 5-6 variables present | 7 or more variables present | |
| M. Emergency Room (ER) Time | ER time 4-6 hours or less | ER time 6-10 hours | ER times 11-20 hours | ER time > 20 hours | |

Page 2 of 5

Pressure, Oxygenation, and Perfusion (POP) Box Factor Assessment

| N. Apparatus | 1 Variable present | 2 Variables present | 3 Variables present | 4 Variables present |
|---|---|---|---|---|
| O. Disease Process<br><br>a. CAD: decreased perfusion systemically and peripherally<br>b. DM: vascular changes<br>c. CHF, CM: Decreased perfusion, vascular stress, decreased oxygenation or stroke volume<br>d. COPD: Smoker-vascular, oxygenation and ventilation effect<br>e. Pulm HTN: decreased oxygenation, possible right to left heart shunt-decreased SaO2, potentially all pulmonary diseases to be added: IPF, CF, by ways of example. All that affects oxygenation (decreased P/F ratios)<br>f. Vascular dx: PVD (decreased perfusion)<br>g. Autoimmune: Vascular collagen changes at a micro vascular level    h. CF: decreased oxygenation at pulmonary level e.g., a decreased SaO2.<br>i. Physical components: micro emboli, nail clubbing<br>j. PE: oxygenation effect-P/F ratio overlap<br>k. Renal Failure: low epogen, low O2 carrying capacity, and/or sudden changes to periphery such as changes in MAP with hemodialysis or | 1 variable present | 2 variables present | 3 variables present | > 4 variables present |

FIG. 1C

Pressure, Oxygenation, and Perfusion (POP) Box Factor Assessment

FIG. 1D

| | | | | |
|---|---|---|---|---|
| CVVHD. L. ESLD: decreased albumin production, decreased oncotic pressures, decreased gluconeogenisis, decreased collagen production. Increased ascites accumulation and fluid shifts. Pleural effusion that can affect oxygenation. Edema effecting stress and tension on skin. A patient with lower B/P in general therefore with decreased MAP effecting decreased perfusion. | | | | |
| P. Steroids | One time yearly for control of disease process | Two times yearly with disease flare | Daily use with disease control | Daily use with disease process not controlled |
| Q. Maceration | Linens or clothing moisture saturated 8 hours | Linen change required q4 hours | Linens changed q2 to maintain skin dryness | Unable to fully stop constant moisture, i.e., greater that +4 edema that has stretched and is now constantly leaking fluids due to impaired integumentary |
| R. Blood Glucose control | Diabetic or medical stressors i.e., steroids but maintains BG equal to 60-120 | BG >120 for more than 8 hours but less than 16 hours | BG>120 for more than 16 hours but less than 24 hours | BG>120 for more than 24 hours |
| S. Hemoglobin/Hematrocrit (H/H) | Hemoglobin 10/Hematocrit 30 | Hgb 9/Hct 27 | Hgb 8/Hct 24 | Hgb 7/Hct 21 |
| T. Length of Stay (LOS) | 1-7 days | 8-14 days | 15-21 days | >21 days |

Pressure, Oxygenation, and Perfusion (POP) Box Factor Assessment

FIG. 1E

| | | | | | |
|---|---|---|---|---|---|
| U. Previous existing skin injury | Old pink previously healed wounds | Reddened areas starting around old wound | Difficulty with O2 and turning and known old wounds | Wounds open again to any stage-progression will be quick | |
| V. Low Albumin | albumin level of 3.5 to more than 3.0 | albumin level 3.0 to more than 2.5 | albumin level 2.5 to more than 2.0 | albumin level less than 2.0 | |
| W. Pressure redistributing surface time line | Regular redistribution bed with Braden < 14 and > 12 for 12 hours | Regular distribution bed with Braden < 12 and > 10 for 12 hour shift | Regular distribution bed with Braden < 10 and > 8 for 12 hour shift | Regular distribution bed with Braden < 8 for 12 hours or greater | |
| X. Pain or paralysis | Patient moves self but must be reminded | Pt must be turned with full assist q2 and mechanical loading | pt must be turned q2 due to immobility but is unstable and can only have 10-20 degree tilt and may not tolerate it. May be associated with recovery and desat time. | Unable to turn to severe pain or severity of critical illness and medical instability. | |
| Y. StO2 measurement | WNL StO2 < 10% of normal | StO2 between 10% and 20% of normal | StO2 between 20% and 30% of normal | StO2 greater than 30% of normal | |
| TOTAL POP FAV ASSESSEMNT | | | | | |

METHOD OF TREATMENT OF PRESSURE RELATED SKIN INJURY

CROSS-REFERENCE TO RELATED APPLICATIONS

This application is a continuation application of co-pending U.S. application Ser. No. 12/793,514 filed on Jun. 3, 2010, which claims the benefit of U.S. Provisional Application No. 61/183,667, filed on Jun. 3, 2009, the disclosures of which are incorporated herein by reference.

FIELD

The present disclosure relates to methods and systems for medical evaluation care and, more specifically, to systems and methods for evaluating a patient for pressure related skin injury risk and recommended treatment.

BACKGROUND

The statements in this section merely provide background information related to the present disclosure and may not constitute prior art.

In medical treatment, pressure ulcers are currently tagged as hospital acquired conditions (HAC) unless they were present on admission (POA) of the patient. When pressure ulcers are classified as HAC, they are almost always considered to be preventable with appropriate treatment. It has been estimated that the cost in the United States for treating stage 3-4 pressure ulcers can be as high as $11 Billion annually. However, the costs for treatment of such patient conditions are withheld per guidelines for pressure ulcers as issued by the Center for Medicare and Medicaid Services (CMS).

The current risk identification tools used most commonly for assessment of patient risk of pressure related skin injury are the Braden and the Norton scale. These tools have become the gold standard for basic risk assessment. However, as described herein, these tools are only the start of the necessary assessment for risk related injury as neither scale addresses the more complex components of critical illness, physiological responses and treatments. All of which have non-visible caustic potential.

While measures should be taken to prevent pressure related injury during medical treatment or a hospital stay, pressure ulcers have been found to occur regardless of strict compliance to preventative measures such as the regular turning of bed ridden patients every two hours, (i.e., turn q2), the redistribution of a patient's weight, mechanical loading and nutritional support. Patients continue to suffer from skin injury even where medical and nursing care is diligent and timely consistent with best practices.

SUMMARY

As addressed herein, the inventor hereof has determined that not all pressure sores or pressure ulcers, even though not initially POA, are purely due to poor nursing care or improper application of medical treatment and found that there are other characteristics and factors that need to be considered when evaluating a patient and providing treatment to a patient. As described herein are new and improved systems and methods for evaluating risk of patients for pressure related injury. These systems and methods can, in some embodiments, provide a more extensive system than currently used and that is inclusive of interrelated variables that can effect integrity of skin or rather the impairment of skin integrity. These variables or factors may be either extrinsic or intrinsic in nature.

As described herein, the Pressure, Oxygenation, and Perfusion (POP) Box (hereinafter "POP Box") systems and methods have been created to expose and apply physiologic factors that lead to skin failure and increased risk of pressure ulcers. In general these intrinsic and/or extrinsic variables and factors have been determined by the inventor to affect pressure, oxygenation or perfusion to skin surface. The POP Box as described herein builds on prior assessments and applies a variety of factors related to the integumentary system, homeostasis and physiological stressors that more fully addresses risks for each patient. The present method and system does not stop or limit itself to the prior risk factors teachings and belief that following the current care practices will prevent pressure ulcers in all cases. The use of the POP Box as described herein utilization, will not by itself prevent all HAC pressure ulcers even with excellent health care, as the inventor hereof has determined that not all HAC pressure ulcers are preventable. For example, it has been determined that some pressure ulcers are the result not of poor nursing care, but are associated with impaired tissue oxygenation that can occur as a result of a large number of factors, other than medical care practitioners following pre-established bedside procedures.

The systems and procedures as described herein are consistent with other evidence based medicine (EBM) procedures for enhancement of health care services. The inventor has determined that it is highly likely that the affects of pressure, oxygenation and perfusion at a microvascular level provide additional variables that can often lead to skin injury. As described herein, underlying health conditions and insults at a micro vascular level can cause and/or hasten skin failure, such as with pressure ulcers. The complex medical conditions that are aggressively and successfully treated may ultimately leave the integumentary system strained. Potential is high for skin insults and/or injuries related to intrinsic responses to constitutional stressors and its treatment. The human body's adaptive responses while seeking homeostasis in stressful situations are often caustic to the skin.

The POP box has been created to expose other insults to patients that can lead to skin failure. In particular, it has been created to identify the extrinsic and intrinsic patient factors leading to skin breakdown and to remove the fault of the nurse in skin injury.

The POP Box system and method as described herein utilize the identified variables that have been determined to affect tissue oxygenation. However, it also recognizes that the measurement of local tissue oxygen saturation (StO2), which can be measured in the tissue microcirculation, will become more common place in the health care environment and as such, the systems and methods described herein will improve the assessment of the risks and prediction of pressure related injury over prior systems and methods. This includes the determination of pressure related injury that occurs from inside the body such as from deep tissue injury, rather than externally applied as previously believed in many cases. As described herein the POP Box can also be named, for example as the "Oxy Bin" illustrating the "bin" or "box" nature of considering the various oxygenation variables in an assessment system and method.

According to one aspect, a system for assessing a patient for pressure related skin injury risk and recommended treatment includes a memory, an input device, an output device, and a processor. The memory and processor include computer executable instructions for implementing the method of receiving a measured pressure on the skin of the patient, and assigning a rating responsive to the received pressure measurement. The method also includes receiving a measured tissue oxygenation of the patient and assigning a rating responsive to the received oxygenation measurement. The method further includes receiving a measured perfusion of the patient and assigning a rating responsive to the received perfusion measurement. The method also includes summing the pressure, tissue oxygenation and perfusion ratings to obtain a POP Box score, determining a risk of pressure related skin injury for the patient in response to the POP Box score and determining a recommended treatment from among a plurality of recommended treatments for the patient in response to the determined risk of pressure related skin injury.

In another aspect, computer readable medium having computer executable instructions for assessing a patient for pressure related skin injury risk and recommended treatment include computer executable instructions performing the method of receiving a measured skin pressure of the patient and assigning a rating responsive to the received skin pressure measurement. The method also includes receiving a measured oxygenation of the patient and assigning a rating responsive to the received oxygenation measurement. The method further includes receiving a measured perfusion of the patient and assigning a rating responsive to the received perfusion measurement. The method also includes summing the skin pressure, oxygenation and perfusion ratings to obtain a POP Box score, determining a risk of pressure related skin injury for the patient in response to the POP Box score. and determining a recommended treatment from among a plurality of recommended treatments for the patient in response to the determined risk of pressure related skin injury.

In yet another aspect, a method for assessing a patient for pressure related skin injury risk and recommended treatment includes measuring skin pressure of the patient and assigning a rating responsive to the skin pressure measurement, measuring tissue oxygenation of the patient and assigning a rating responsive to the tissue oxygenation measurement, and measuring perfusion of the patient and assigning a rating responsive to the perfusion measurement. The method also includes summing the skin pressure, tissue oxygenation and perfusion ratings to obtain a POP Box score, determining a risk of pressure related skin injury for the patient in response to the POP Box score, and determining a recommended treatment from among a plurality of recommended treatments for the patient in response to the determined risk of pressure related skin injury.

According to another aspect, such methods can include measuring skin pressure of the patient and assigning a rating responsive to the skin pressure measurement, measuring oxygenation of the patient and assigning a rating responsive to the oxygenation measurement, measuring perfusion of the patient and assigning a rating responsive to the perfusion measurement, summing the skin pressure, oxygenation and perfusion ratings to obtain a POP Box score, determining a risk of pressure related skin injury for the patient in response to the POP Box score, and determining a recommended treatment from among a plurality of available recommended treatments for the patient in response to the determined risk of pressure related skin injury.

In accordance with another aspect, a system or method for assessing a patient for pressure related skin injury risk and recommended treatment including measuring StO2 in the patient and assigning a first StO2 rating where StO2 levels of WNL SO2 are less than 10 percent of normal; assigning a second StO2 rating where StO2 is between 10 and 20 percent of normal; assigning a third StO2 rating where StO2 is between 20 and 30 percent of normal; and assigning a fourth StO2 rating where StO2 is greater than 30 percent of normal.

The method also includes summing the assigned ratings to obtain a POP Box score, and determining a risk of pressure related skin injury for the patient in response to the POP Box score, and determining or selecting a recommended treatment from among a plurality of recommended treatments for the patient in response to the determined risk of pressure related skin injury.

In yet another aspect, a system or method for assessing a patient for pressure related skin injury risk and recommended treatment including evaluating the patient based on a review of various factors and assigning a rating responsive to the evaluations including measuring StO2 in the patient and assigning a rating responsive to the StO2 measurement. The method can also include one or more of the following additional processes: determining an age of the patient and assigning a rating responsive to the determining; determining a body mass index of the patient and assigning a rating responsive to the determining; determining whether the patient was found in a down position prior to evaluation and assigning a rating responsive to the determining; determining an operating room variable of the patient wherein in the assigning is responsive to the number of such operating room variables present; determining a presence of one or more disease processes present in the patient wherein in the assigning is responsive to the number of such disease processes are present; determining steroid use by the patient and assigning a rating responsive to the determining; determining LOS for both ICU and regular hospital stays for the patient and assigning a rating responsive to the determining; determining a pressure redistribution surface time of the patient and assigning a rating responsive to the determining; determining a presence of pain or paralysis of the patient and assigning a rating responsive to the determining; measuring a vital sign of the patient including the blood pressure and heart rate and assigning a rating responsive to the measuring; measuring a venous oxygen saturation (SvO2) or central venous oxygen saturation (SvcO2) and assigning a rating responsive to the measuring; measuring a ratio of arterial oxygen concentration to the fraction of inspired oxygen (referred commonly as the P/F ratio) of the patient and assigning a rating responsive to the measuring; measuring a desaturation recovery time oxygen saturation (SpO2) or oxygen attached to the haemoglobin cell in the circulatory system of a patient and assigning a rating responsive to the measuring; measuring a cardiac index (CI), cardiac output (CO) and/or Stroke Volume (SV) of the patient and assigning a rating responsive to the measuring; measuring an Edema of the patient and assigning a rating responsive to the measuring; measuring a blood glucose of a patient and assigning a rating responsive to the measuring; measuring a hemogolin/hematocrit (H/H) of the patient and assigning a rating responsive to the measuring; measuring a Albumin level of the patient and assigning a rating responsive to the measuring; identifying a presence of one or more pressor agents and assigning a rating responsive to the identifying; evaluating an emergency room procedure experience by the patient and assigning a rating responsive to the evaluating; identifying a presence of one or more mechanical apparatus associated with the patient wherein in the assigning is responsive to the number of identified apparatus present; identifying maceration can include identifying moisture content of linens and clothing of the patient and assigning a rating responsive to the identifying; and identifying previous or existing skin injury of the patient and assigning a rating responsive to the identifying; summing the assigned ratings from the Braden Score and the StO2 measurement to obtain a POP Box score, determining a risk of pressure related skin injury for the patient in response to the POP Box score, wherein the ratings for each factor is from 1 to 4, and wherein determining a recommended treatment for the patient in response to the determined risk of pressure related skin injury wherein the POP Box score is 0 to 25, take no action; wherein the POP Box score is 25 to 50, provide normal turn on redistributing surface practice; wherein the POP Box score is 50 to 75, adapt patient care for low air loss overlay or surface with constant air redistribution; wherein the POP Box score is between 75 and 100, provide patient with a low air loss bed, provide a more frequent turn schedule and/or continual turn bed; and wherein the POP Box score is greater than 100, provide patient with a low air loss bed with continual turning.

Further aspects of the present disclosure will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

FIGS. 1A-1E are collectively a chart of the Pressure, Oxygenation, and Perfusion (POP) Box system and method according to one exemplary embodiment of the disclosure.

It should be understood that throughout the drawings, corresponding reference numerals indicate like or corresponding parts and features.

DETAILED DESCRIPTION

Figure 2:
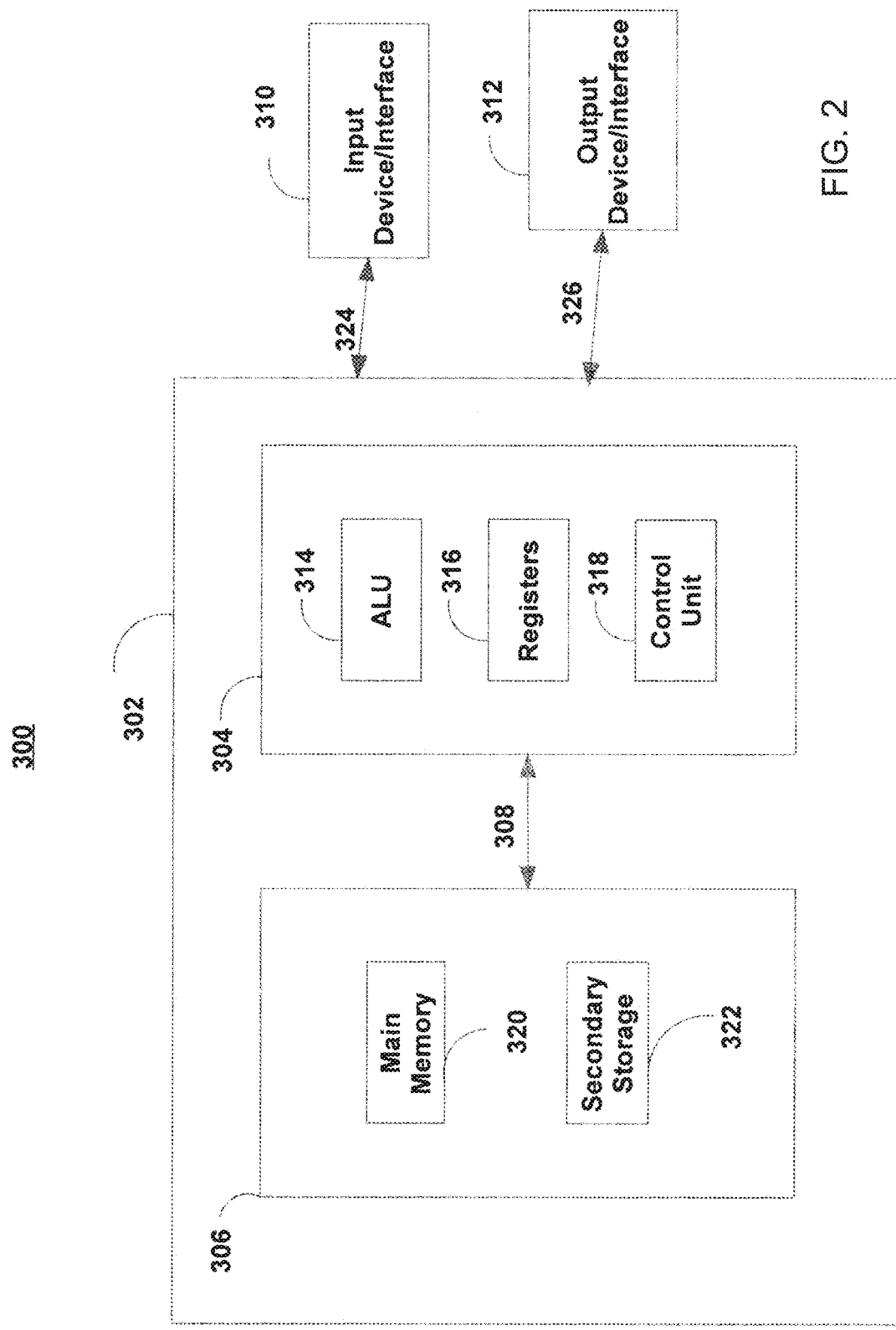
FIG. 2 is a block diagram of a computer system that may be used to implement one or more exemplary embodiments and/or one or more components or modules of the Pressure, Oxygenation, and Perfusion (POP) Box system and method as described herein.

The following description is merely exemplary in nature and is not intended to limit the present disclosure or the disclosure's applications or uses.

Before turning to the figures and the various exemplary embodiments illustrated therein, a detailed overview of various embodiments and aspects is provided for purposes of breadth of scope, context, clarity, and completeness.

According to one embodiment, a system or method for assessing a patient for pressure related skin injury risk and recommended treatment including measuring skin pressure of the patient and assigning a rating responsive to the skin pressure measurement, measuring oxygenation of the patient and assigning a rating responsive to the oxygenation measurement, measuring perfusion of the patient and assigning a rating responsive to the perfusion measurement, summing the pressure, oxygenation and perfusion ratings to obtain a POP Box score, determining a risk of pressure related skin injury for the patient in response to the POP Box score, and selecting or determining a recommended treatment for the patient in response to the determined risk of pressure related skin injury. As discussed herein, skin pressure or sometimes just pressure refer to intrinsic and extrinsic forces that are applied to the skin that can result in injury to the skin resulting from such forces.

As noted above, while the process herein includes selecting and/or determining a recommended treatment, nothing in this present disclosure or claims specifically identifies the particular treatments based on the POP Box scores or in anyway limits or restricts those treatments. The determined recommended treatments of the present systems and methods are determined using the POP Box scores from the experience of the medical care providers and by standards that can be determined overall time based on the best practices in the medical profession as determined in view of the determined POP Box scores. Such determined recommended treatments can vary by medical care provider and are expected to change over time.

A risk of pressure related skin injury is determined for the patient in response to the POP Box score. A recommended treatment for the patient is then selected in response to the determined risk of pressure related skin injury. This later can include, but is not limited to, assigning ratings on a scale of 1 to 4 and taking no action with the POP Box score is 0 to 25, but where the POP Box score is 25 to 50, provide normal turn on redistributing surface practice, the POP Box score is 50 to 75, adapt patient care for low air loss overlay or surface with constant air redistribution, the POP Box score is between 75 and 100, provide patient with a low air loss bed, provide a more frequent turn schedule and/or continual turn bed; and where the POP Box score is greater than 100, provide patient with a low air loss bed with continual turning.

Of course, one skilled in the art will understand that additional factors can also be considered and still be within the scope of the present disclosure. These can include one or more of the following factors, alone or in additional combinations. It should also be understood that the rating of 1 to 4 for each is only one exemplary embodiment. Each factor can have more or less ratings and each may have a different rating range or weighting and still be within the scope of the present disclosure.

The method can include evaluating the patient using Braden Scale to obtain a Braden Score and assigning a rating from 1 to 4 responsive to the Braden Score. the Braden Score can be included in the POP Box score for evaluation and selection of the treatment for the patient.

Of course, additional factors in addition to the Braden scale score and the measurement of tissue oxygenation such as by measurement of local tissue oxygen saturation (StO2) by measurement of the microcirculation in the tissue using an StO2 monitoring device), can be utilized according to the present methods and systems. StO2 as a measurement of tissue oxygenation can be measured in the microcirculation where oxygen is exchanged with tissue such as by continuous measurement/monitoring of peripheral perfusion, as known to those of skill in the art.

As one example of the StO2 rating, the method provides for assigning a first StO2 rating where StO2 levels of WNL SO2 are less than 10 percent of normal; assigning a second StO2 rating where StO2 is between 10 and 20 percent of normal; assigning a third StO2 rating where StO2 is between 20 and 30 percent of normal; and assigning a fourth StO2 rating where StO2 is greater than 30 percent of normal. As StO2 monitoring becomes more widely available to medical personnel that may be due in part to its significant benefit in analyzing pressure ulcer risks, the variables as identified herein and their various determined numerical value assignments can provide medical care personnel with a significant improvement in medical diagnosis and improved patient care.

The method can include one or more of the following processes that can be included as factors in predicting pressure sore risk and in determining appropriate recommended treatments. These can include one or more of:

a. determining whether the patient was found in a down position prior to evaluation and assigning a rating responsive to the determining;

b. determining an operating room variable of the patient wherein in the assigning is responsive to the number of such operating room variables present; determining a presence of one or more disease processes present in the patient wherein in the assigning is responsive to the number of such disease processes are present;

c. determining steroid use by the patient and assigning a rating responsive to the determining;

d. determining LOS for both ICU and regular hospital stays for the patient and assigning a rating responsive to the determining;

e. determining a pressure redistribution surface time of the patient and assigning a rating responsive to the determining; determining a presence of pain or paralysis of the patient and assigning a rating responsive to the determining;

f. measuring a vital sign of the patient including the blood pressure and heart rate and assigning a rating responsive to the measuring (such as heart rate (HR); Systolic blood pressure (SBP); diastolic blood pressure (DBP); and mean arterial pressure (MAP));

g. measuring a venous oxygen saturation (SvO2) or central venous oxygen saturation (SvcO2) and assigning a rating responsive to the measuring;

h. measuring a P/F ratio (the ratio of arterial oxygen concentration to the fraction of inspired oxygen) of the patient and assigning a rating responsive to the measuring;

i. measuring a desaturation recovery time of an oxygen saturation (SpO2) of the patient and assigning a rating responsive to the measuring;

j. measuring a Cardiac Index (CI) or Cardiac Output (CO) of the patient and assigning a rating responsive to the measuring;

k. measuring an Edema of the patient and assigning a rating responsive to the measuring;

l. measuring a blood glucose of a patient and assigning a rating responsive to the measuring; measuring a hemogolin/hematocrit (H/H) of the patient and assigning a rating responsive to the measuring;

m. measuring a Albumin level of the patient and assigning a rating responsive to the measuring;

n. identifying a presence of one or more pressor agents and assigning a rating responsive to the identifying;

o. evaluating an emergency room procedure experience by the patient and assigning a rating responsive to the evaluating;

p. identifying a presence of one or more mechanical apparatus associated with the patient wherein in the assigning is responsive to the number of identified apparatus present;

q. identifying maceration, that can include identifying moisture content of linens and clothing of the patient, for example, and assigning a rating responsive to the identifying; and r. identifying previous or existing skin injury of the patient and assigning a rating responsive to the identifying;

It would be understood to those of skill in the art that these factors are only representative factors and that other factors may also be identified and rated and included in the overall POP Box score for use in determining treatment plans for patients. While not listed for instance, the gender and race of the patient may be additional factors in some embodiments. As noted, not all of the factors are necessarily and a subset of the factors are possible and expected in some embodiments. Additionally, as StO2 is a relatively new measureable characteristic that has been identified as one POP Box factor, other new patient measurements and characteristics are also possible in the future as technology and medical understanding for diagnosis develops. These new diagnosis variables can be included in other embodiments and are considered to be within the scope of the present disclosure.

1. Patient Diagnosis

In some embodiments, the Pressure, Oxygenation, and Perfusion (POP) Box (POP Box) system and method can include all or a portion of the following evaluation factors and POP Factor Assessment Value (POP FAV) (in this example of assigning a rating from 1 to 4 for each factor). It should be understood to those skilled in the art that one or several of these factors may not be applicable to a particular patient and therefore not applicable to the current system and method, generally on a patient by patient basis.

2. Exemplary POP Box Factors and Weightings

The following exemplary POP Box Factor analysis addresses 25 exemplary intrinsic and extrinsic factors, some or all of them can be included in the POP Box as may be determined suitable for particular uses and as determined overtime by a medical care practitioner. This example allocates each of these into four categories for ratings and assignment of ratings. Of course one skilled in the art will understand that a more or less granular rating assignment scheme can also be employed and still be within the scope of the present disclosure and claims.

A. Braden Scale: As the prior art use of the Braden Scale For Predicting Pressure Sore Risk can decrease the risk for associated pressure injury increases. In one embodiment, a POP Factor weighting assignment includes as one factor a Braden Scale assessment having different POP Box categories allocations for factor weighting: a first for a Braden score of 17-15; a second for a Braden score of 14-12; a third for a Braden score of 12-10; and a fourth for a Braden score of 9 and below.

B. Patient Age: As a person ages the subcutaneous layer is decreased due to less collagen production. The collagen composition is affected due to a decrease in intrinsic hormone mediators (usually estrogen), that therefore decreases the production of collagen. With less collagen in the subcutaneous tissue, there is a decrease in surface area protection and elasticity. Regarding vasculature, though collateral circulation is more defined in the older person the possibility for oxygenation to be compromised is increased as well. With the increase of age exposure to CAD pressure ulcer risk causing factors are also increased. The POP Factor B Weighting Assignment of the patient's age into the four exemplary categories can include the following, one category classification for each of: a first for an age range of 20-40 years old; a second for an age range of age 40-60 years old; a third for an age range of age 60-80 years old; and a fourth for an age of older than 80.

C. Body Mass Index (BMI): The following factors are considered as increased risk factors associated with an increased BMI: HTN, Dyslipidemia, DM2, CAD, and Sleep Apnea, according to some embodiments. All of these conditions can be associated with perfusion or oxygenation compromise. Increasing risk for damage from oxygen deprivation at the peripheral vascular level. A different POP Factor for a weighting assignment of the BMI can include: a first for a normal weight but Body Mass Index compromised below 2; a second for an underweight where the weight is more than 18.5 under normal; a third for an overweight condition such as when the weight is between 25-29.9 above normal; and a fourth for an obese weight of a BMI of 30 or greater.

D. Found Down: When a patient has been found down, deep tissue injury is suspected to happen from interface forces. The longer the contact time of immobility on a hard surface the greater the increased risk of decreased tissue perfusion and oxygenation thus increasing risk of deep tissue injury. This injury takes hours to days to appear. Therefore, the fact that a patient is found down after a fall has not been previously considered a risk factor, however, this is included here as having been determined to be another POP Box factor. The POP Factor for weighting assignment for the factor of the patient being found in a down position can include: a first when found down for short period of time less than 1 hour; a second when found down between 1 to 2 hours wherein the ph and lactate may/or may not be affected; a third when found down between 2 to 5 hours and wherein a ph measurement is down and lactate is identified as being elevated; and a fourth when found down greater than 5 hours and where the measured ph is down and lactate is up, with potentially MB-CPK (creatine phosphokinase-MB (CPK-MB)) is up. The CPK-MB measurement is a cardiac marker often used to assist diagnoses of an acute myocardial infarction.

E. Vital signs: Vital signs can include the patient's heart rate (HR); Systolic blood pressure (SBP); diastolic blood pressure (DBP); and/or mean arterial pressure (MAP). This can also include instability such as Tachycardia and Hypotension. With decrease in blood pressure (B/P), it would be assumed that tissue perfusion and ultimately tissue oxygenation are effected. When increased HR atrial kick is lost, cardiac output is decreased and potential for a decrease in perfusion state exists. There is a potential for 20% of blood volume (stroke volume) to be lost. Increased skin temperature can improve perfusion but increases in temperature increases oxygen consumption. Furthermore a febrile state may increase vasodilatation and skins perfusion but rigors in this febrile state will increase oxygen consumption (VO). Conversely, hypothermia would simply represent decreased perfusion due to vasoconstriction and decreased tissue perfusion. The POP Factor weighting assignment for measured vital signs can include an allocation to four categories, for example: a first for HR within normal levels (WNL), SBP<90 DBP<60, MAP<60; a second for HR>100, SBP<85 DBP<50, MAP <55; a third for HR>120, SBP<70 DBP<45, MAP<50; and a fourth for HR in/out >140, SBP 70 or less with tacky: DBP and MAP critically low. These of course can change and the categorization made more complex with various combinations of measurements.

F. Pressor Agents: With the use of vaso active agents to enhance cardiac output and brain and heart perfusion, it is known that the periphery is vasoconstricted to increase cardiac return, thus, blood volume is taken from the periphery to the core. This factor addresses the caustic affects to the integument system by those known vasoconstriction agents. The POP Factor weighting assignment for identified or measured pressor agents can include: a first for Dopamine at 5 mcg/kg/min or Levophed 5-10 mcg/min; a second for Dopamine 10-15 mcg/kg/min or Levophed 10-15 mcg/min; a third for Dopamine 15-25 mcg/kg/min or Levophed 15-25 mcg/min; and a fourth for Dopamine ineffective or Levophed >25 mcg/min.

G. SvO2 or ScvO2: A venous oxygen saturation (SvO2) or central venous oxygen saturation (ScvO2) represents the venous return side. Correlation of tissue oxygenation and extraction are interrelated. Poor (low or very high SvO2) can represent limited oxygen extraction. It may also represent limited oxygen carrying capacity. At this time, SvO2 is the closest number for tissue oxygenation/extraction known. Different shock states will have variable SvO2 values but are expected to have the same effect to the skin. While measurement of the change in the SvO2 is often not available due to its invasiveness, when available to be measured, it can contribute useful information regarding systemic oxygenation delivery and consumption. The POP Factor weighting a for assignments for measured venous oxygen saturation (SvO2) or central venous oxygen saturation (ScvO2) can include: a first for a measured SvO2<60 or >75; a second for a measured SvO2 of 40-50 cardiogenic/75-80 septic shock; a third for a measured SvO2<40 cardiogenic/80-90 septic shock; and a fourth for a measured SvO2<30 cardogenic shock/>90 septic shock.

H. P/F Ratio: The ratio of arterial oxygen concentration to the fraction of inspired oxygen (P/F ratio) can also be a factor as a decreasing P/F ratio, e.g., PaO2/FiO, may indicate the capability to upload oxygen to hemoglobin is affected. Therefore, P/F ratio measurement can assist with assessment of factors affecting oxygenation at all levels. The POP Factor weighting assignment for the P/F Ratio can include: a first for a P/F ratio 280-250; a second for a P/F ratio 250-200; a third for a P/F ratio 200-150; and a fourth for a P/F ratio of less than 150.

I. Desaturation Recovery time (Oxygen Saturation SpO2=90 or >): When turning and moving the critically ill patient there will be periods of desaturation with various recovery time with position changes and other procedures. This comes from the movement of blood in areas of shunts and changes in DO2 and VO2. Patients left sedentary are potentially more affected. However an increase in recovery time would represent the decrease in tissue perfusion. Separate consideration can be provided when SpO2 is less than 90, for example. The POP Factor weighting assignment for SpO2 can include: a first for a recovery time of 1-2 minutes; a second for a recovery time of 2-5 minutes; a third for a recovery time of 5-10 minutes; and a fourth for a recovery time of greater than 10 minutes J. CO/CI/SV: With the decrease in cardiac function tissue, perfusion is affected, thus tissue oxygenation. Evaluation of the cardiac output, the cardiac index and/or the stroke volume (SV) can be indicative and instructive. Poor EF and Poor SV will result in a decrease in distal tissue perfusion. As CI goes down, the Stroke Volume (SV) will increase thus potentiating decreased tissue oxygenation at peripheral locations. The POP Factor weighting assignment for Cardiac Output (CO) and/or Cardiac Index (CI) can include: a first for CI-2.5 BNP>100 or SV>60; a second for CI<2.0 BNP>200 or 60<SV>55; a third for CI<1.5 BNP>500 or 55<SV>50; and a fourth for CI<1.0 BNP>800 or SV<50.

K. Massive edema: The massive edema can include -Sepsis fluid resuscitation, acute renal failure (ARF), and low albumin. During critical illness, the body's homeostatic mechanisms lead to fluid retention. The body can swell more that 4+ anascarca by retaining extra fluids. In fact, the body can hold liters of extra fluid and stretch the integumentary system that can result in cracking and blistering of the skin. At such points of failure, weeping will start and constant moisture expulsion will ensue. Additionally, maceration and deterioration to the skin will happen. When both albumin and oncotic pressure are low, fluid shifts to a third space. This can create a possible shunt between oxygen and the skin and can also increase the surface area required for perfusion in an already compromised perfusion state. The POP Factor weighting assignment for edema can include: a first for Edema considered to be +1 mm with finger compression; a second for Edema considered to be +2 mm with finger compression; a first for Edema considered to be +3 mm with finger compression; and a fourth for Edema considered to be +4 or greater with finger compression.

L. Operating Room Procedure: With any invasive procedure there are variables that effect tissue oxygenation and perfusion. Skin would be more vulnerable to stress related injury. During surgery, a prolonged period of immobility exists similar to the "found down" factor yet in a monitored environment. However, variable conditions occur in the operating room (OR) contributing to an increased risk of skin breakdown. These can include one or more of the following: a. time on OR table >4 hours-especially w/o pressure reducing device; b. Chilling of core temp—decrease bleeding; c. Not placed on pressure reducing surface while reperfusion; d. Drop of MAP <55; e. Use of Neo stick or presser agent to recover B/P; f. Use of Heart-Lung bypass machine; g. PAR instability; and/or h. excessive bleeding (can be defined by way of example as bleeding greater than 6 U of PRBC's required in a 24 hour perioperative period). The POP Factor weighting assignment for the operating room procedures can include: a first where 1-2 variables are present or identified; a second wherein 3-4 variables are present; a third where 5-6 variables are present; and a fourth where there are 7 or more variables present.

M. Emergency Room (ER) Time: A patient can have an extensive stay while awaiting treatment and a room. Often there is no pressure redistributing device either for chairs or stretchers. Additionally, trauma patients are on a hard backboard. As a result, the amount of time until treatment needs to be considered. The POP Factor weighting assignment for ER time can include: a first for an ER time of 4-6 hours or less; a second for an ER time of 6-10 hours; a third for an ER time of between 11-20 hours; and a fourth for an ER time greater than 20 hours.

N. Apparatus With added apparatus of hard surfaces applied to the body there is likelihood of interface surface pressure. This would cause decreased perfusion, decreased oxygenation and true pressure to a surface. Furthermore, when mechanically loading it is more challenging to redistribute pressures with added weight and bulk. The apparatus factors can include the presence of each of the following as being one apparatus variable: Splint, traction, cervical collar, RPM machine, pins/rods, balloon pump, VAD, external pacemaker, and cast. For example, 2 casts+one external pacemaker=3 variables. The POP Factor weighting assignment for patient apparatus can include: a first for one apparatus variable being present; a second where there are 2 apparatus variables present; a third where there are 3 apparatus variables present; and a fourth where there are 4 or more variables present.

O. Disease Process: The reality of underlying disease process effecting perfusion and oxygenation is not accounted for with current risk assessment tools. With the advent of deep tissue injury (NPUAP) the understanding that injury can occur from the inside out is now understood. It has been determined that there are diseases that predispose skin to injury more quickly. Those that involve decrease perfusion and oxygenation at the tissue level are considered as such, but also can include those that involve decreased sensory and movement capability including those having a neurological effect. The possible disease process factors or variables can include: a. CAD: decreased perfusion systemically and peripherally; b. DM: vascular changes; c. CHF, CM: Decreased perfusion, vascular stress; d. COPD: Smoker-vascular, oxygenation and ventilation effect; e. Pulm HTN: decreased oxygenation, possible right to left heart shunt-decreased SaO2, potentially all pulmonary diseases to be added: IPF, CF, by ways of example. All that affects oxygenation (decreased P/F ratios); f. Vascular dx: PVD; g. Autoimmune: Vascular collagen changes at a micro vascular level; h. CF: decreased oxygenation at pulmonary level e.g., a decreased SaO2; i. Physical components: micro emboli, nail clubbing; j. PE: oxygenation effect-P/F ratio overlap; k. Renal Failure: low epogen, low O2 carrying capacity, and/or sudden changes to periphery such as changes in MAP with hemodyalysis or CVVHD; l. ESLD: decreased albumin production, decreased oncotic pressures, decreased gluconeogenisis, decreased collagen production. Increased ascites accumulation and fluid shifts. Pleural effusion that can affect oxygenation. Edema effecting stress and tension on skin. A patient with lower B/P in general therefore with decreased MAP effecting decreased perfusion. The POP Factor weighting assignment can include: a first where one variable are present; a second where 2 variables are present; a third where 3 variables are present; and a fourth where 4 or more variables are present.

P. Steroids: With vascular compromise the body mounts an inflammatory response to help bring added nutrition and vascular elements to the affected area. With chronic immunosuppression, the body is unable to mount the natural inflammatory response for wound healing. With chronic steroid use there is also a decrease of Estrogen production that causes a decrease in collagen production and its protective layer at the subcutaneous layer. The POP Factor weighting assignment to consider the patient's use of steroids can include: a first category for one time yearly use for control of a disease process; a second for two times yearly with disease flare; a third for daily use with disease control; and a fourth where daily use with disease process not controlled.

Q. Maceration: As skin becomes macerated the integrity of the skin is threatened. Separation of epidermis from dermis in these moisture states increases the potential for skin breakdown. This is not only through incontinence and perspiration but also physiological responses such as to deprave. The POP Factor weighting assignment for identification of maceration can include: a first where linens or clothing moisture are saturated q8 hours; a second for linen change required q4 hours; a third for linens changed q2 to maintain skin dryness; and a fourth where it is not possible to fully stop constant moisture i.e., greater that +4 edema that has stretched and is now constantly leaking fluids due to impaired integumentary R. Blood Glucose: Cellular activity is most functional when availability of Insulin for cellular activity (enzymatic transport) is kept at appropriate levels. Insulin being the most important factor for active transport in blood glucose (BG) utilization. Well balanced glucose control facilitates ATP synthesis, thus providing necessary factors for protein utilization, cellular response to stress i.e., inflammatory process and aiding in the healing process. (Reconstructive phase). Thus, glucose control provides better response overall to the stress of disease process, allowing for stronger effective responses to all stressors. This factor may need to be assessed by HgB AlC regulation as well as albumin synthesis. The POP Factor weighting assignment can include: a first for a diabetic or medical stressors i.e., steroids but maintains BG equal to 60-120; a second for a BG>120 for more than 8 hours but less than 16 hours; a third for a BG>120 for more than 16 hours but less than 24 hours; and a fourth for a BG>120 for more than 24 hours.

S. H/H: Low Hemoglobin /Hematocrit (H/H) represents low oxygen caring capacity leading to decreased oxygen delivery and potentially tissue oxygenation is affected. Potentially low H/H is not represented well by StO2 measurement. Massive losses quickly will affect oxygen caring capacity. The POP Factor weighting assignment for Hemoglobin/Hematocrit (H/H) can include: a first for Hemoglobin 10/Hematocrit 30; a second for Hgb 9/Hct 27; a third for Hgb 8/Hct 24; and a fourth for Hgb 7/Hct 21.

T. Length of Stay (LOS): Increasing length of stay (LOS) both ICU and regular hospital increases chances of iatrogenic injury. There is a higher risk for infection, need for more procedures and constitutional stressors. Nutrition is often compromised by NPO status for tests. The POP Factor weighting assignment for length of stay can include: a first where the length of stay is 1-7 days, a second where it is 8-14 days; a third where it is 15-21days; and a fourth is greater than 21 days.

U. Previous existing skin injury: Previously existing wounds will only effectively heal to 80% of original strength. Thus less tolerance to new injury and stressors. Decreased tissue strength, potentially of all layers. The POP Factor weighting assignment can include: a first where old pink previously healed wounds are present; a second where there are reddened areas starting around an old wound; a third where therein is difficulty with O2 and turning and known old wounds; and a fourth where wounds open again to any stage-progression will be quick.

V. Albumin: Albumin holds oncotic pressure. From the dietary standpoint measurement of albumin is not a fair indicator of nutrition in a stress r/t situation due to the massive consumption and inability to use or synthesize prealbumin. However to note the concentration will quickly indicate oncotic hold. When Alb is low and fluid third spaces "water sits" between vessel and tissue. Thus, creating QS/QT at tissue level. Not allowing for distant tissue oxygenation. Also, perpetuating skin stretching effect, thinning it and increasing the stretch and strain from inside to out. The POP Factor weighting assignment can include: a first where the albumin level is 3.5 to more than 3.0; a second where the albumin level is 3.0 to more than 2.5; a third where the albumin level is 2.5 to more than 2.0; and a fourth where the albumin level is less than 2.0.

W. Pressure redistributing surface time line: A decrease in Braden leads to a result in surface reassessment with a possible change. (i.e., Computerized Graphing). If surfaces are not appropriate for medical condition and changes there could be additional external caustic factors. In this case, not decreasing surface area pressure. With the StO2 device the measurement of PSI and surface redistribution will be measurable and ascertainable. The POP Factor weighting assignments can include a first where there is a regular redistribution bed with Braden<14 and >12 for 12 hours; a second where there is a regular distribution bed with Braden<12 and >10 for 12 hour shift; a third where there is a regular distribution bed with Braden<10 and >8 for 12 hour shift; and a fourth where there is a regular distribution bed with Braden<8 for 12 hours or greater.

X. Pain or paralysis: Critically ill patients may not move in response to pain to decreased sensation of pain or weakness. Critically ill patients may be unable to redistribute weight at all due to chemically induced paralysis or a physiologic paralysis due to injury or illness, either factor impairs movement and direct interface forces may be extensive in time. The POP Factor weighting assignment can include: a first where the patient moves himself or herself but must be reminded; a second where the patient must be turned with full assist q2 and requires mechanical loading; a third where the patient must be turned q2 due to immobility but is unstable and can only have 10-20 degree tilt and may not tolerate it and or may be associated with recovery and desat time; and a fourth where the patient is unable to turn due to severe pain or severity of critical illness and medical instability.

Y. StO2: StO2 can provide for the measurement and/or early detection of oxygen deprivation at a tissue level. StO2 measurement can indicate O2 delivery and consumption imbalance, but does not measure O2 consumption. Measurement of StO2 can aid in the identification of early stages of tissue injury at a micro capillary level, by measuring changes as they occur. This can aid in the earlier identification of the "at risk group." StO2 can illustrate the pathway of skin failure, time line, cause, and affects and aid in the application of appropriate equipment and measurable measures and evaluation thereof. StO2 can aid in the identification of the invisible offenders that decrease tissue oxygenation by capturing the changes at the microcirculation level of the patient. The POP Factor weighting assignment for StO2 can include: a first for StO2 levels of WNL SO2 are less than 10 percent of normal; a second for StO2 is between 10 and 20 percent of normal; a third for StO2 is between 20 and 30 percent of normal; and a fourth for StO2 is greater than 30 percent of normal.

Some of the potential benefits of measuring StO2 levels of WNL established can include StO2 vs. O2 consumption. Variables that may need to be considered will be core and skin temp. Also, reperfusion time, surface and temp measurement. Especially after OR. Another one is StO2 Extraction /shunt. This can cause a false sense of comfort. *StO2–ScVo2 (SVO2)=true tissue extraction. In any high flow state i.e.: sepsis or ESLD the StO2 levels will potentially be elevated or WNL due to a hyper dynamic state. O2 extraction is decreased due to increased FTC (Velocity). In essence creating a shunt effect. This is currently supported with increased Lactate levels and decreased ph, and elevated CPK. These measurements support the idea of anaerobic oxygenation-lack of O2 at tissue level. As should be known to those of skill in the art after reading this disclosure, the uses of continuous StO2 are innumerable. These can include: ER-found down, hypotensive, hemorrhage; OR—anesthesia induction-sedation, neostick-B/P control manipulation, Bypass ICU-Pressers, CVVHD, edema, instability and inability to mobilize pt, ARDS; Wound clinic-Wound healing, Una boot application; All shock states-with possible exception of neuroleptic HD, drastic changes in tissue perfusion with large changes in circulating volume is believed to affect StO2. Similarly, the response of vasoconstriction at peripheral level and oxygen carrying capacity with decreased volume also is believed to affect StO2.

StO2 measurement can provide evidence based medicine (EBM) of a measured amount that will quantify as oxygen deprivation thus creating injury from inside out, e.g., deep tissue injury. Once fully available, the measurement of StO2 will help in conjunction with the system and method as described herein and will illustrate the pathway of skin failure, time line, cause and effect, appropriate equipment usage there will be measurable numbers to the invisible offenders that decrease tissue oxygenation. Caustic events and factors that can result in pressure ulcers in patients, even where appropriate medical care is provided in a competent and timely manner, will be identifiable on a per patient basis and can aid in the development of new or modified patient care procedures.

3. Exemplary Assessment of Overall Assigned POP Box Weighting Value

After the applicable, some or all or a portion thereof, of the above various intrinsic and extrinsic factors have been reviewed and assigned a weight according to the above description, an overall POP Box Score or Value is determined by summing up all of the assigned weighted assignments. For example, where all 25 factors are considered, as shown in FIG. 2, the following care analysis can be implemented, as just one example, based assigning factors from 1 to 4 to the above 26 factors. Where the POP Box score is 0 to 25, the determined medical treatment may be that no action or treatment specific for the treatment or prevention of ulcers is required or needs to be taken. Where the weighted total patient score of 25 to 50, a determined or selected medical treatment for the prevention and treatment of ulcer's may include providing a normal turn process for the patient based on redistributing surface practice, i.e., versacare. Where the total weighted patient score is 50 to 75, a medical care provider may determine that there is a moderate risk of the patient developing pressure ulcers. In such cases, the patient's care may be adapted such that there is a low air loss overlay or surface with constant air redistribution i.e., sofcare w/pump, provided to the patient. Where the total weighted patient score is between 75 and 100, the medical care professional may determine there is a high risk for skin r/t injury. In such cases, the medical care provider may adjust the patient's treatment to anticipate the development of pressure ulcers and as such, the patient may be provided with a low air loss bed, a more frequent turn schedule and/or continual turn bed, possibly based on staff availability. Where the total weighted patient score is greater than 100, the medical care provider may determine a medical treatment for the patient may include providing the patient with a low air loss bed and with continual turning. Such determinations can also be included in medical supporting software based on predetermined criteria and ratings and aid in providing the medical care professional with recommended treatments.

Of course, it should be understood by one skilled in the art and practice as a health care provider, that these ranges and the implications of these ranges can be adjusted and still be within the scope of the present disclosure.

As understood to those in the art having reviewed this present disclosure, the systems and methods described herein and claimed or claimable by this disclosure, provide a medical aid to healthcare and medical practitioners. Nothing in this present disclosure or claims specifically identifies the particular recommended treatments based on the POP Box scores or in anyway limits or restricts those recommended treatments. The determined recommended treatments of the present systems and methods are determined using the POP Box scores from the experience of the medical care providers and by standards that can be determined overall time based on the best practices in the medical profession as determined in view of the determined POP Box scores. Such determined treatments can vary by medical care provider and are expected to change over time.

4. Benefits in Various Embodiments Over the Prior Art

The POP box can improve medical diagnosis and treatment for a variety of medical conditions and needs. The POP Box systems and methods as described herein can, in some embodiments, help to expose variables, events and conditions that are caustic to skin integrity that have not previously been considered as risk factors. The POP Box system and methods can in other embodiments, help guide the prevention and care required with the increase in risk factors such as changes in medical treatment equipment and modification to patient turn schedules. In other embodiments, the POP Box system and method can potentially increase medical care provider patient interventions for guiding appropriate staffing needs for advanced preventative care. In some other embodiments, the POP Box system and method can establish, or help the care givers establish, a fixed set of risk variables that can be utilized for risk assessment and allocation by various stakeholders, by quantifying and organizing the factors so they can be understood and tabulated. In other embodiments, the POP Box system can establish factors or help the care giver in establishing the factors, assessment and guidelines for determining the severity of particular patient status or underlying illness and conditions for inclusion in assessing medical treatments and life lengthening decisions.

5. POP Box Exemplary System Embodiment

Figure 3:
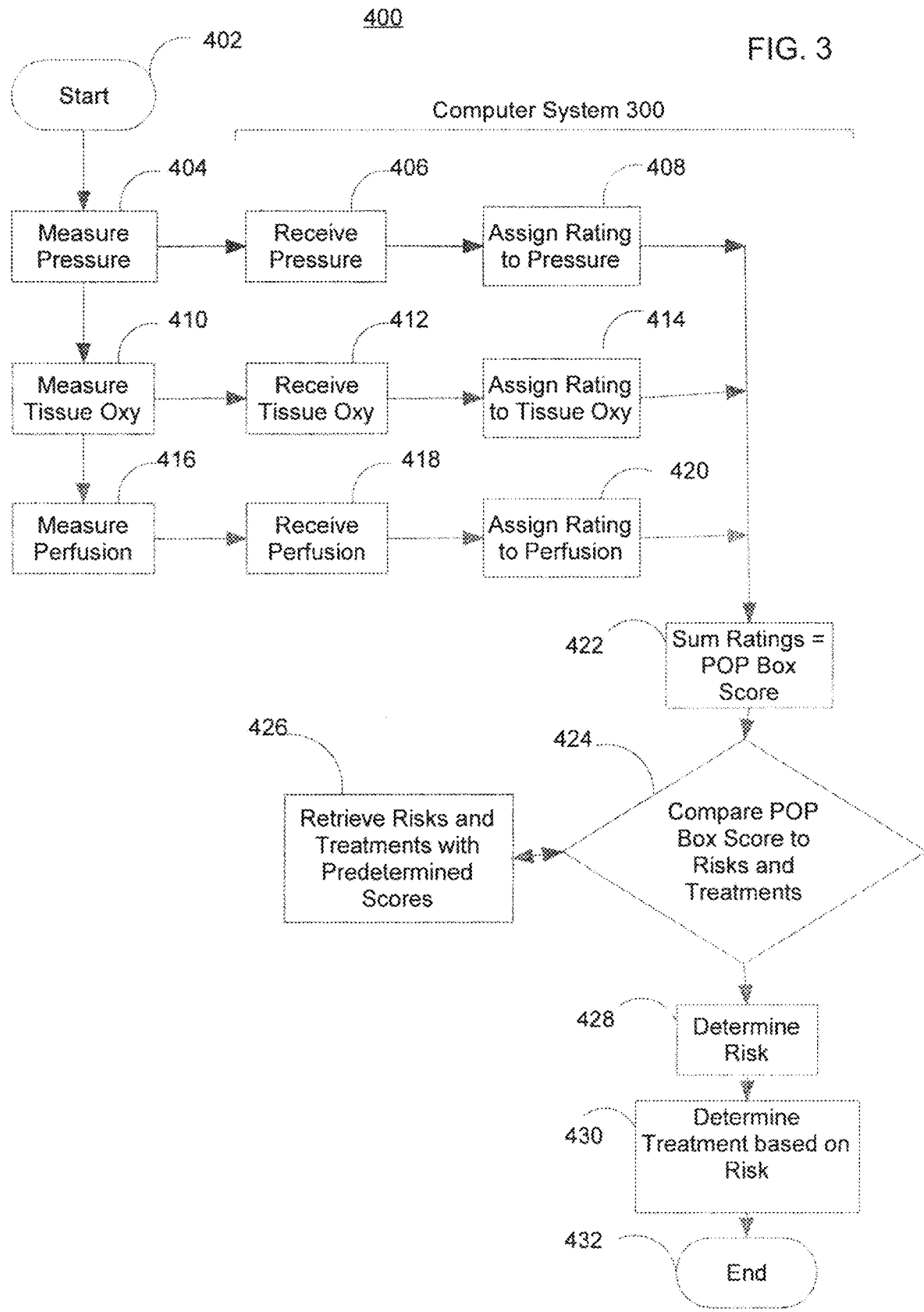
FIG. 3 is a flow chart diagram of a method for assessing a patient for pressure related skin injury risk and recommended treatment according to one exemplary embodiment.

As will be understood to one skilled in the art, the POP Box system and method as described herein can be implemented in whole or in part in an automated manner, including within a computer system or systems, and in particular as computer implemented instructions having computer executable instructions for performing some or all of the methods disclosed herein. Referring to FIG. 3, an operating environment for an exemplary embodiment of a Pressure, Oxygenation, and Perfusion (POP) Box system and method including one or more components or modules thereof is a computer system 300 with a computer 302 that comprises at least one high speed processing System (CPU) 304, in conjunction with a memory system 306 interconnected with at least one bus structure 308, an input device 310, and an output device 312. These elements are interconnected by at least one bus structure 312.

The illustrated CPU 304 is of familiar design and includes an arithmetic logic unit (ALU) 314 for performing computations, a collection of registers 314 for temporary storage of data and instructions, and a control System 316 for controlling operation of the system 300. Any of a variety of processors, including at least those from Digital Equipment, Sun, MIPS, Motorola, NEC, Intel, Cyrix, AMD, HP, and Nexgen, is equally preferred for the CPU 304. The illustrated embodiment of the system operates on an operating system designed to be portable to any of these processing platforms.

The memory system 306 generally includes high-speed main memory 320 in the form of a medium such as random access memory (RAM) and read only memory (ROM) semiconductor devices, and secondary storage 322 in the form of long term storage mediums such as floppy disks, hard disks, tape, CD-ROM, flash memory, etc. and other devices that store data using electrical, magnetic, optical or other recording media. The main memory 320 also can include video display memory for displaying images through a display device. Those skilled in the art will recognize that the memory system 306 can comprise a variety of alternative components having a variety of storage capacities and can include a subscriber identity or information module (SIM) such as a GSM SIM Card, in one embodiment.

The input device 310 and output device 312 are also familiar. The input device 310 typically comprises a keyboard, but can also include a mouse, a touch screen, a physical transducer (e.g. a microphone), etc. and is interconnected to the computer 302 via an input interface 324. The output device 312 can comprise a display but can also include a printer, a transducer (e.g. a speaker), etc, and be interconnected to the computer 302 via an output interface 326. Some devices, such as a network adapter or a modem, can be used as input and/or output devices.

As is familiar to those skilled in the art, the computer system 300 further includes an operating system and at least one application program. The operating system is the set of software which controls the computer system's operation and the allocation of resources. The application program is the set of software that performs a task desired by the user, using computer resources made available through the operating system. Both are resident in the illustrated memory system 306.

In accordance with the practices of persons skilled in the art of computer programming, the present system is described below with reference to symbolic representations of operations that are performed by the computer system 300. Such operations are sometimes referred to as being computer-executed. It will be appreciated that the operations which are symbolically represented include the manipulation by the CPU 304 of electrical signals representing data bits and the maintenance of data bits at memory locations in the memory system 306, as well as other processing of signals. The memory locations where data bits are maintained are physical locations that have particular electrical, magnetic, or optical properties corresponding to the data bits. The system can be implemented in a program or programs, comprising a series of instructions stored on a computer-readable medium. The computer-readable medium can be any of the devices, or a combination of the devices, described above in connection with the memory system 306.

Referring now to FIG. 4, a method for assessing a patient for pressure related skin injury risk and recommended treatment is illustrated. As shown in this exemplary embodiment, the method starts 402 with a measurement of a patient's skin pressure 404. The measured skin pressure is input at 406 into a computer system such as system 300 via an input device 310 and stored in memory 306. The system 300 includes computer implementable instructions for assigning a rating in 408 to skin pressure based on predetermined allocations such as those described above by way of example. The assigned skin pressure rating of 408 is also stored in memory 306. The tissue oxygenation of the patient is measured in 410 and entered and received by system 300 in 412. The system assigned a tissue oxygenation rating in 414 and both the measured tissue oxygenation and the assign tissue oxygenation rating are stored in memory 306. The perfusion is measured in 416 and received by the system 300 in 418. The system 300 assigns a perfusion rating in 420. Both the measured perfusion and the assigned perfusion rating are stored in memory 306. Of course one skilled in the art will understand that the order of processes 404 to 420 can be changed in any manner and still be within the scope of the present method. Additionally, as described above, these three variables of skin pressure, tissue oxygenation, and perfusion are exemplary variables or factors. Additional or different variables and factors can be implemented by some embodiments of the method and still be within the scope of the present disclosure.

Next the system 300 sums the available factor ratings in 422 to determine a POP Box Score. Of course, while summing is identified as one method or algorithm for determining the POP Box Score, those skilled in the art will understand that other methods and algorithms can be utilized to determine the POP Box Score of the various selected and/or included factors and still be within the scope of the present disclosure. The total POP Box Score is provided to a comparison process of 424 for comparison to determine the risks to the patient for pressure related skin injury and determining a recommended treatment. A plurality of risks for pressure related skin injury and recommended treatments are predetermined and scored by medical professionals and stored in memory 306. Each of these risks and recommended treatments can include one or more assigned POP Box Score. The patient's POP Box score of process 422 is compared in process 424 with the predetermined or allocated ratings obtained from process 426 in process 428 and a recommended treatment is determined in 430 based on the comparison process 424 and the determined risk of 428. The determined recommended treatment of 430 can be presented to the medical care provider as an output of the system 300 such as inclusion in a report or as a presentation at the output interface 312. The medical care provider can be presented with the determined risk 428 and recommended treatment 430 and can also be presented with some or all of the stored measurements and assigned ratings for final selection by the medical care provider of the treatment of the patient. The determined recommended treatment is also stored in memory 306. The process ends at 432.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. A method of treatment for prevention of pressure related skin injury in a patient by a caregiver of the patient comprising:

receiving a plurality of predefined weighted ratings for each of a plurality of factors including skin pressure, tissue oxygen saturation (StO2), and perfusion factors, wherein the plurality of StO2 predefined weighted ratings is weighted in a different weighting range than the weighted rating range for skin pressure and perfusion, each predefined weighted rating being associated with one or more different predefined measurement value for each factor;

receiving a plurality of Pressure, Oxygenation, and Perfusion (POP) Box (POP Box) scores and an associated skin injury risk and a recommended treatment for each;

receiving a measured skin pressure of the patient;

comparing the received measured skin pressure with the received predefined measurement values for skin pressure;

assigning a skin pressure weighted rating responsive to the comparing of the received skin pressure measurement with the received predefined measurement values for skin pressure, wherein the assigned weighted rating is the predefined weighted rating associated with the comparable predefined measurement value for the received measured skin pressure;

receiving a measured tissue oxygen saturation (StO2) of the patient;

comparing the received measured tissue oxygen saturation (StO2) with the received predefined measurement values for tissue oxygen saturation (StO2);

assigning a tissue oxygen saturation (StO2) weighted rating responsive to the comparing of the received measured tissue oxygen saturation (StO2) with the received predefined measurement values for tissue oxygen saturation (StO2), wherein the assigned weighted rating is the predefined weighted rating associated with the comparable predefined measurement value for the received measured tissue oxygen saturation (StO2);

receiving a measured perfusion of the patient;

comparing the received measured perfusion with the received predefined measurement values for perfusion;

assigning a perfusion weighted rating responsive to comparing of the received perfusion measurement with the received predefined measurement values for perfusion, wherein the assigned weighted rating is the predefined weighted rating associated the comparable predefined measurements value for the received measured perfusion;

summing the assigned skin pressure, tissue oxygen saturation (StO2) and perfusion weighted ratings to determine a POP Box score;

determining a risk of pressure related skin injury for the patient in response to comparing the determined POP Box score to the received predefined POP Box scores and identification of the associated received predefined skin injury risk;

determining a recommended treatment responsive to comparing at least one of the POP Box score and the determined risk of pressure related skin injury to the associated received predefined recommended treatments;

communicating the determined recommended treatment to the caregiver;

receiving by the caregiver the determined recommended treatment for the patient; and performing the received determined recommended treatment in the treatment of the patient for the prevention of pressure related skin injury.

2. The method of claim 1 wherein the received predefined weighted ratings with the associated predefined measurement value and the assigning of the tissue oxygen saturation (StO2) weighted rating based on StO2 includes:

a first StO2 weighted rating where StO2 levels of within normal levels (WNL) StO2 are less than 10 percent of normal;

a second StO2 weighted rating where StO2 is between 10 and 20 percent of normal;

a third StO2 weighted rating where StO2 is between 20 and 30 percent of normal; and a fourth StO2 weighted rating where StO2 is greater than 30 percent of normal.

3. The method of claim 1 further comprising:

receiving a measurement of a venous oxygen saturation (SvO2) or a central venous oxygen saturation (SvcO2) and the comparing thereof and the assigning of the tissue oxygenation weighted rating being based on the measured SvO2 or SvcO2;

receiving a measurement of a ratio of arterial oxygen concentration to the fraction of inspired oxygen (P/F ratio) of the patient and wherein the assigning of the tissue oxygen saturation (StO2) weighted rating is responsive to the measured P/F ratio;

receiving a measurement of a desaturation recovery time of oxygen saturation (SpO2) of the patient and wherein the assigning of the tissue oxygenation weighted rating is responsive to the measured desaturation recovery time of SpO2;

receiving a measurement of a blood glucose of a patient and wherein the assigning of the tissue oxygen saturation (StO2) weighted rating is responsive to the measured blood glucose;

receiving a hemoglobin/hematocrit (H/H) measurement of the patient and wherein the assigning of the tissue oxygen saturation (StO2) weighted rating responsive to the measured H/H;

receiving a measured vital sign of the patient including the blood pressure and heart rate and wherein the assigning of the tissue oxygen saturation (StO2) weighted rating is responsive to the measured vital sign;

receiving a Cardiac Index (CI), Cardiac Output (CO), or Stroke Volume (SV) measurement of the patient and wherein the assigning of the tissue oxygen saturation (StO2) weighted rating is responsive to the received measured CI, CO or SV;

receiving a measured or identified presence of one or more pressor agents and wherein the assigning of the tissue oxygen saturation (StO2) weighted rating is responsive to the measured or identified pressor agent; and receiving an identified maceration of the patient and wherein the assigning of the tissue oxygen saturation (StO2) weighted rating is responsive to the identified maceration.

4. The method of claim 1, further comprising:

determining a Braden Score and the assigning the skin pressure weighted rating responsive to the Braden Score;

determining an age of the patient and wherein the assigning of the skin pressure weighted rating responsive to the determining of the age;

receiving a determined presence of steroid use by the patient and wherein the assigning of the skin pressure weighted rating is responsive to the determining of the presence of steroid use;

receiving a measured Edema of the patient and wherein the assigning of the skin pressure weighted rating responsive to the measuring of the Edema;

receiving a determined presence of pain or paralysis of the patient and wherein the assigning of the skin pressure weighted rating responsive to the determining of the present of pain or paralysis;

receiving a measured Albumin level of the patient and wherein the assigning of the skin pressure weighted rating responsive to the measuring of the Albumin level;

receiving an identified presence of one or more mechanical apparatus associated with the patient and wherein the assigning of the skin pressure is responsive to the number of identified apparatus present; and receiving a determined pressure redistribution surface time of the patient and wherein the assigning of the skin pressure weighted rating responsive to the determining.

5. The method of claim 1, further comprising one or more of the following processes:
   receiving a measured vital sign of the patient including the blood pressure and heart rate and wherein the assigning of the perfusion weighted rating responsive to the received measured vital sign;
   receiving a measured Cardiac Index (CI), Cardiac Output (CO), or Stroke Volume (SV) of the patient and wherein the assigning of the perfusion weighted rating is responsive to the received measured cardiac measurement;
   receiving an identified presence of one or more pressor agents and wherein the assigning of the perfusion weighted rating responsive to the received identified pressor agent; and
   receiving an identified maceration of the patient and wherein the assigning of the perfusion weighted rating is responsive to the received identified maceration.

6. The method of claim 1, further comprising one or more of the following processes:
   receiving a determined body mass index of the patient and assigning a body mass index weighted rating to the received body mass index is responsive to the received determined body mass index;
   receiving a determination of whether the patient was found in a down position prior to evaluation and assigning a down position weighted rating responsive to the received determination of patient found in a down position;
   receiving a plurality of determined operating room variables of the patient and assigning an operating room weighted rating responsive to the number of such operating room variables received;
   receiving a determined presence of one or more disease processes present in the patient and assigning a disease process presence weighted rating responsive to the number of received present disease processes;
   receiving a determined length of stay for both ICU and regular hospital stays for the patient and assigning a hospital length of stay weighted rating responsive thereto;
   receiving an evaluation of an emergency room procedure experience by the patient and assigning an emergency room procedure experience weighted rating responsive thereto ; and
   receiving an identified previous or existing skin injury of the patient and assigning a preexisting skin injury weighted rating responsive thereto
   and wherein the summing to determine the POP Box score further includes the assigned weighted rating for the one or more above additional received factors.

7. The method of claim 1 wherein the weighted rating range for skin pressure and perfusion is a rating value from 1 to 4; and
   wherein the POP Box score is determined to be in the range of 0 to 25, the determined and communicated recommended treatment is taking no action;
   wherein the POP Box score is determined to be in the range of 25 to 50, the determined and communicated recommended treatment is providing normal turn on redistributing surface practice;
   wherein the POP Box score is determined to be in the range of 50 to 75, the determined and communicated recommended treatment is adapting care of the patient for low air loss overlay or surface with constant air redistribution;
   wherein the POP Box score is determined to be in the range of 75 to 100, the determined and communicated recommended treatment is providing the patient with a low air loss bed, providing a more frequent turn schedule and/or providing for continual turn bed; and
   wherein the POP Box score is determined to be greater than 100, the determined and communicated recommended treatment is providing the patient with a low air loss bed with continual turning.

8. The method of claim 1, further comprising:
   repeating the treatment steps of receiving, comparing, and assigning for each of the skin pressure, tissue oxygen saturation (StO2) and perfusion and the steps of summing, determining the risk, and determined the recommended treatment until the POP Box score is in a no treatment range; and
   when it is determined that the determined treatment is in the no treatment range, taking no further action for the prevention of pressure related skin injury.

9. The method of claim 1 wherein the weighted rating range for skin pressure and perfusion is a rating value from 1 to 4.

10. The method of claim 1 wherein:
    the POP Box score is determined to be in a first treatment range, the determined recommended treatment is providing normal turn on redistributing surface practice;
    the POP Box score is determined to be in a second treatment range, the determined recommended treatment is adapting care of the patient for low air loss overlay or surface with constant air redistribution;
    the POP Box score is determined to be in a third treatment range, the determined recommended treatment is providing the patient with a low air loss bed, providing a more frequent turn schedule and/or providing for continual turn bed;
    the POP Box score is determined to be in a fourth treatment range, the determined recommended treatment is providing the patient with a low air loss bed with continual turning; and
    the POP Box score is determined to be in a no treatment range, the method provides for taking no further action for prevention of pressure related skin injury.

11. The method of claim 10 wherein
    wherein the no treatment range is where the determined POP Box score is in the range of 0 to 25;
    wherein the first treatment range is where the determined POP Box score is in the range of 25 to 50;
    wherein the second treatment range is where the determined POP Box score is in the range of 50 to 75;
    wherein the third treatment range is where the determined POP Box score is in the range of 75 to 100; and
    wherein the fourth treatment range is where the determined POP Box score is greater than 100.

12. The method of claim 1
    wherein the POP Box score is determined to be in the range of 25 to 50, the determined and communicated recommended treatment is providing normal turn on redistributing surface practice;
    wherein the POP Box score is determined to be in the range of 50 to 75, the determined and communicated recommended treatment is adapting care of the patient for low air loss overlay or surface with constant air redistribution;
    wherein the POP Box score is determined to be in the range of 75 to 100, the determined and communicated recommended treatment is providing the patient with a low air loss bed, providing a more frequent turn schedule and/or providing for continual turn bed;
wherein the POP Box score is determined to be greater than 100, the determined and communicated recommended treatment is providing the patient with a low air loss bed with continual turning; and
wherein the POP Box score is determined to be less than 25, taking no action for the prevention of pressure related skin injury.

13. A method of treatment for prevention of pressure related skin injury in a patient by a caregiver of the patient comprising:
receiving predefined weighted ratings for each of a plurality of factors including skin pressure, tissue oxygen saturation (StO2), and perfusion factors, each predefined weighted rating being associated with one or more different predefined measurement value for each factor wherein the plurality of StO2 predefined weighted ratings is weighted in a different weighting range than the weighted rating range for skin pressure and perfusion;
receiving a plurality of Pressure, Oxygenation, and Perfusion (POP) Box (POP Box) scores and an associated skin injury risk and a recommended treatment for each;
receiving a measured skin pressure of the patient;
comparing the received measured skin pressure with the received predefined measurement values for skin pressure;
assigning skin pressure a weighted rating responsive to the comparing of the skin pressure measurement with the received predefined measurement values for skin pressure, wherein the assigned weighted rating is the predefined weighted rating associated with the comparable predefined measurement value for the received measured skin pressure;
receiving a measured tissue oxygen saturation (StO2) of the patient;
comparing the measured tissue oxygen saturation (StO2) with the received predefined measurement values for tissue oxygen saturation (StO2);
assigning a tissue oxygen saturation (StO2) weighted rating responsive to the comparing of the measured tissue oxygen saturation (StO2) with the received predefined measurement values for tissue oxygen saturation (StO2), wherein the assigned weighted rating is the predefined weighted rating associated with the comparable predefined measurement value for the received measured skin pressure;
receiving a measured perfusion of the patient;
comparing the received measured perfusion with the received predefined measurement values for perfusion;
assigning a weighted rating responsive to the comparing of the perfusion measurement with the received predefined measurement values for perfusion, wherein the assigned weighted rating is the predefined weighted rating associated the comparable predefined measurements value for the received measured perfusion;
summing the assigned skin pressure, tissue oxygen saturation (StO2) and perfusion weighted ratings to determine a POP Box score;
determining a risk of pressure related skin injury for the patient in response to comparing the determined POP Box score to the received predefined POP Box scores and identification of the associated received predefined skin injury risk;
determining a recommended treatment responsive to comparing at least one of the POP Box score and the determined risk of pressure related skin injury to the associated received recommended treatments,
wherein the POP Box score is determined to be in a first treatment range, the determined recommended treatment is providing normal turn on redistributing surface practice;
wherein the POP Box score is determined to be in a second treatment range, the determined recommended treatment is adapting care of the patient for low air loss overlay or surface with constant air redistribution;
wherein the POP Box score is determined to be in a third treatment range, the determined recommended treatment is providing the patient with a low air loss bed, providing a more frequent turn schedule and/or providing for continual turn bed; and
wherein the POP Box score is determined to be in a fourth treatment range, the determined recommended treatment is providing the patient with a low air loss bed with continual turning;
wherein the POP Box score is determined to be in a fifth treatment range, which is a no treatment range wherein the recommended treatment is to take no action for the prevention of pressure related skin injury;
communicating over the output interface the determined recommended treatment;
receiving by the caregiver the determined recommended treatment for the patient;
performing the received determined recommended treatment in the treatment of the patient for the prevention of pressure related skin injury; and
repeating the treatment steps of receiving, comparing, and assigning for each of the skin pressure, tissue oxygen saturation (StO2) and perfusion and the steps of summing, determining the risk, and determined the recommended treatment, until the determined POP Box score is in the no treatment range wherein the method provides for taking no action for the prevention of pressure related skin injury.

14. The method of claim 13 wherein the assigning of the tissue oxygen saturation (StO2) weighted rating based on StO2 is a function of the received predefined weighted ratings with the associated predefined measurement value and includes:
a first StO2 weighted rating where StO2 levels of within normal levels (WNL) StO2 are less than 10 percent of normal;
a second StO2 weighted rating where StO2 is between 10 and 20 percent of normal;
a third StO2 weighted rating where StO2 is between 20 and 30 percent of normal; and
a fourth StO2 weighted rating where StO2 is greater than 30 percent of normal.

15. The method of claim 13, further comprising one or more of the following:
a measured a venous oxygen saturation (SvO2) or a central venous oxygen saturation (SvcO2) and receiving a plurality of SvO2 or SvcO2 predefined measurement values and the comparing thereof and assigning a venous oxygen saturation (SvO2) or a central venous oxygen saturation (SvcO2) weighted rating being based on the measured SvO2 or SvcO2;
a measured a ratio of arterial oxygen concentration to the fraction of inspired oxygen (P/F ratio) of the patient and assigning an arterial oxygen concentration to the fraction of inspired oxygen (P/F ratio) weighted rating is responsive to the measured P/F ratio;

a measured a desaturation recovery time of oxygen saturation (SpO2) of the patient and assigning a desaturation recovery time of oxygen saturation (SpO2) weighted rating is responsive to the measured desaturation recovery time of SpO2;

a measured a blood glucose of a patient and assigning of a blood glucose weighted rating is responsive to the measured blood glucose;

a measured a hemoglobin/hematocrit (H/H) of the patient and assigning a hemoglobin/hematocrit (H/H) weighted rating responsive to the measured H/H;

a measured vital sign of the patient including the blood pressure and heart rate and assigning a vital sign weighted rating is responsive to the measured vital sign;

a measured a Cardiac Index (CI), Cardiac Output (CO), or Stroke Volume (SV) measurement of the patient and assigning a Cardiac Index (CI), Cardiac Output (CO), or Stroke Volume (SV) weighted rating is responsive to the received measured CI, CO or SV;

an identified presence of one or more pressor agent and assigning a pressor agent weighted rating is responsive to the identified pressor agent; and an identified maceration of the patient and assigning a maceration weighted rating is responsive to the identified maceration.

16. The method of claim 13, further comprising one or more of the following processes:

receiving a determined Braden Score and wherein assigning the skin pressure weighted rating is responsive to the received Braden Score;

receiving an age of the patient and assigning the skin pressure weighted rating is responsive to the received age;

receiving a determined steroid use by the patient and assigning the skin pressure weighted rating is responsive to the received determined steroid use;

receiving a measured Edema of the patient and assigning the skin pressure weighted rating is responsive to the received measured Edema;

receiving a determined a presence of pain or paralysis of the patient and assigning the skin pressure weighted rating is responsive to the received determined presence of pain or paralysis;

receiving a measured Albumin level of the patient and assigning the skin pressure weighted rating is responsive to the received measured Albumin level;

receiving an identified presence of one or more mechanical apparatus associated with the patient wherein the assigning the skin pressure is responsive to the number of identified apparatus present; and receiving a determined pressure redistribution surface time of the patient and assigning the skin pressure weighted rating is responsive to the received determined pressure redistribution surface time.

17. The method of claim 13, further comprising one or more of the following processes:

receiving a measured vital sign of the patient including the blood pressure and heart rate and assigning the perfusion weighted rating is responsive to the received measured vital sign;

receiving a measured Cardiac Index (CI), Cardiac Output (CO), or Stroke Volume (SV) of the patient and assigning the perfusion weighted rating is responsive to the received measured Cardiac Index (CI), Cardiac Output (CO), or Stroke Volume (SV);

receiving an identified presence of one or more pressor agent and assigning the perfusion weighted rating is responsive to the received identified pressor agent; and receiving an identified maceration of the patient and assigning the perfusion weighted rating is responsive to the received identified maceration.

18. The method of claim 13, further comprising one or more factor processes selected from the group consisting of:

receiving a determined body mass index of the patient and assigning a weighted rating responsive to the received body mass index;

receiving a determination that patient was found in a down position prior to evaluation and assigning a found down weighted rating responsive thereto;

receiving a determination of an operating room variable of the patient and assigning an operating room variable weighted rating responsive to the number of such operating room variables present;

receiving a determination of a presence of one or more disease processes present in the patient and assigning a present disease weighted rating responsive to the number of such present disease processes;

receiving a determination of a length of stay for both ICU and regular hospital stays for the patient and assigning a hospital length of stay weighted rating responsive thereto;

receiving a determination of an evaluation of an emergency room procedure experience by the patient and assigning an emergency room procedure experience weighted rating responsive to the received determined evaluation ; and identifying previous or existing skin injury of the patient and assigning a preexisting skin injury weighted rating responsive to the identifying;

and wherein the summing to determine the POP Box score further includes the assigned weighted rating for these one or more factor processes.

19. The method of claim 13 wherein the weighted rating range for skin pressure and perfusion is a rating value from 1 to 4.

20. The method of claim 13 wherein wherein the no treatment range is where the determined POP Box score is in the range of 0 to 25;

wherein the first treatment range is where the determined POP Box score is in the range of 25 to 50;

wherein the second treatment range is where the determined POP Box score is in the range of 50 to 75;

wherein the third treatment range is where the determined POP Box score is in the range of 75 to 100; and wherein the fourth treatment range is where the determined POP Box score is greater than 100.

* * * * *